United States Patent [19]

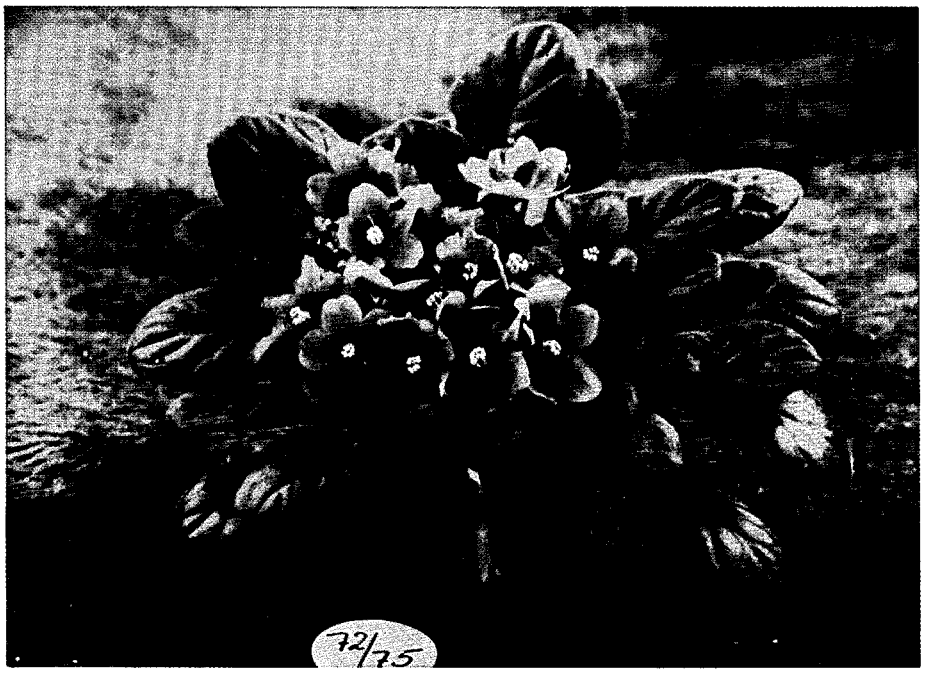
72/75

Holtkamp

[11] Plant 4,213

[45] Feb. 14, 1978

[54] AFRICAN VIOLET PLANT

[76] Inventor: Reinhold Holtkamp, Weatherstrasse 112, 4294 Isselburg, Germany

[21] Appl. No.: 743,149

[22] Filed: Nov. 18, 1976

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

An African violet plant having purple-red, star shaped flowers on strong, erect peduncles to form a large, solid flower head above the foliage, with flowering being continuous.

2 Drawing Figures

The present invention comprises a new and distinct cultivar of African violet plant, botanically known as *Saintpaulia ionantha,* and hereafter referred to by the cultivar name Delaware.

Delaware, referred to during the selection process by the designation Type 72/76 is a product of a planned breeding program which had the objective of creating a new African violet cultivar with red, star-shaped flowers, upright strong stems, large and non-dropping flowers, intensive color, and compact habit. These traits in combination were not present in previously available commercial cultivars of African violets.

The new cultivar was originated from a cross made in a controlled breeding program in Isselburg, Rhineland, Germany. The female, or seed parent was an unpatented cultivar identified by the breeding No. XIX 4082. The male, or pollen parent was an unpatented variety having star-shaped flowers and identified by the breeding No. XIX 4394. The male parent has upright and relatively strong stems and 6–10 star-shaped flowers.

The new cultivar Delaware was discovered and selected as a flowering plant within the progeny of the stated cross by me in controlled environment in Isselburg, Rhineland, Germany. Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following observations, measurements and values describe plants grown in Isselburg, Rhineland, Germany, under greenhouse conditions which closely approximate those generally used in commercial practice.

The following traits have been repeatedly observed and are determined to be basic characteristics of Delaware which in combination distinguish this African violet as a new and distinct cultivar:

1. Very upright and strong flower stems which rigidly support the large flowers.
2. Compact plant which can be grown close together without stretching leaf stems.
3. Flowers very uniformly and approximately 6–8 weeks after potting.
4. Continuous productivity of new flowers.
5. Red, large star-shaped flowers which are non-dropping.

In the accompanying photographic drawings,

FIG. 1 comprises a perspective view of the plant, and

FIG. 2 is a photograph showing various parts of the plant, top and underside, and the developing bud formations. The colors appearing in the photographs are as true as possible with color illustrations of this type.

In the following description, color references are made to the Horticultural color chart issued by Wilson Colour Ltd., except where general color terms of ordinary significance are obvious. The accompanying photographic drawing shows a typical specimen plant of the new cultivar, with the colors appearing in the photograph being as true as possible with color illustrations of this type.

Botanical classification: *Saintpaulia ionantha,* Ramat. cv. Delaware.

Parentage:

*Male parent.*—XIX 4394, star-shaped, generally pink flower color, 628/2.

*Female parent.*—XIX 4082, red.

Propagation: The new cultivar holds its distinguishing characteristics through successive propagations by leaf cuttings and by division of shoots.

Plant: From 8 cm. to 10 cm. tall when grown in pots, and approximately 22 cm. in diameter when fully grown.

*Leaves.*—General form: heart-shaped. Diameter: 6–7 cm. Texture: soft. Aspect: velvety and hairy. Veins: from underside, well pronounced, green to reddish. Color (upperside): parsley green 00962. Color (underside): erythrite red 0027/2. Petiole: green to reddish.

Flowers:

*Buds.*—Cup-shaped, 10 mm. before opening; brownish, very hairy 4–5 weeks from visible to opening of flower.

Sepals.—Color: Garnet brown 00918. Calyx: Funnel-shaped and synsepelous. Aspect: Hairy, spear-shaped. Peduncle: 4–6 cm. green to reddish, erect.

Individual flowers:

*Size.*—45–50 mm. in diameter.

*Color.*—Upperside: Ranges between 71A and 71B, with the color photographic drawing showing the flower color somewhat more blue than the actual flower color; center is darker and is velvety. Underside: Approximately 71C.

*Borne.*—Symetrical; star-shaped with 5–7 uniform sepals.

*Shape.*—Most with six sepals, first cup-shaped, then becoming flat when fully open.

*Corolla.*—5–7 connected petals with darker center; upperside velvety, underside gooseskin-like.

*Arrangement.*—Erect flower-stem, dark brown, ending on the receptacle (torus) connected by the brown spear-shaped sepals.

Flowering time: The new variety will show first flowers approximately 6 weeks after potting and can be brought again to bloom in a cycle of 4–6 weeks.

Reproductive organs:

*Stamens.*—5–6.

*Anthers.*—Two cells, each cell 2 mm. long and 1 mm. wide; color is canary yellow 2.

*Arrangement.*—Basifixed, 5–6 in number, each composed of two anther cells; 10–12 in each blossom.

*Filaments.*—4–5 mm. long, color canary yellow 2/2.

*Styles.*—7–8 mm. long, color violet purple 733/1.

*Pollen color.*—Canary yellow 2/1.

Roots: Well developed root system, white when young and active, turning to brownish color on older plant.

Disease resistance: Excellent resistance shown to date to mildew, botrytis and soft-rot.

General observations: This plant is a very vigorous type and comes uniformly in bloom approximately 5–6 weeks after potting. Erect, upright peduncles at the end of strong stems, with 6–9 stalks each 6–8 cm. long coming out of the center of the plant. The stalks are strong and each carry 4–6 large red flowers 40–55 cm. in diameter and star-shaped, which do not drop from the stems after withering thereby avoiding damage and destruction due to botrytis from fallen blossoms. The plant bears a large, solid, flower head 8–10 cm. in diameter, the flower head being above a wreath of medium green leaves on each plant surrounding the flower.

I claim:

1. A new and distinct cultivar of African violet known by the cultivar name Delaware and particularly characterized as to uniqueness by the combined characteristics of upright and strong stems each of which supports 4–6 large flowers which are red in flower color and star-shaped; uniform flowering and compact growth habit, with continuous productivity of new flowers.

* * * * *

UNITED STATES PATENT OFFICE
CERTIFICATE OF CORRECTION

PATENT NO. : PP-4213

DATED : February 14, 1978

INVENTOR(S) : REINHOLD HOLTKAMP

It is certified that error appears in the above-identified patent and that said Letters Patent are hereby corrected as shown below:

In column 1, cancel the last three lines in their entirety.

In column 2, cancel the first two lines in their entirety, and in place of the cancelled matter at the bottom of column 2 and the first two lines of column 2, insert --The accompanying photographic drawing shows a typical specimen plant of the new cultivar, with the colors appearing in the photograph being as true as possible with color illustrations of this type.--

In column 2, cancel the sentence beginning in line 6 and ending in line 10, namely, "The accompanying photographic drawing shows a typical specimen plant of the new cultivar, with the colors appearing in the photograph being as true as possible with color illustrations of this type."

In column 2, line 6, change the period to a comma and insert after the comma --and except for the color values for the upperside and underside of the flowers, which are from RHS Colour Chart, 1966 Edition--.

Signed and Sealed this

*Twenty-sixth* Day of *September 1978*

[SEAL]

*Attest:*

RUTH C. MASON
*Attesting Officer*

DONALD W. BANNER
*Commissioner of Patents and Trademarks*